(12) United States Patent
Edic et al.

(10) Patent No.: US 7,082,180 B2
(45) Date of Patent: *Jul. 25, 2006

(54) METHODS AND APPARATUS FOR COMPUTING VOLUMETRIC PERFUSION

(75) Inventors: Peter Michael Edic, Albany, NY (US); Samit Kumar Basu, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 223 days.

This patent is subject to a terminal disclaimer.

(21) Appl. No.: 10/724,461

(22) Filed: Nov. 26, 2003

(65) Prior Publication Data

US 2004/0111023 A1    Jun. 10, 2004

Related U.S. Application Data

(63) Continuation-in-part of application No. 10/304,380, filed on Nov. 26, 2002, now Pat. No. 6,888,914.

(51) Int. Cl.
*A61B 6/00* (2006.01)
(52) U.S. Cl. .......................... 378/4; 378/901
(58) Field of Classification Search ............ 378/4, 378/19, 62, 98.11, 98.12, 901; 382/130, 382/131, 132; 385/132; 600/420, 425, 431
See application file for complete search history.

(56) References Cited

U.S. PATENT DOCUMENTS

| 5,070,877 | A | 12/1991 | Mohiuddin et al. | 600/420 |
|---|---|---|---|---|
| 5,339,817 | A | 8/1994 | Nilsson | 600/473 |
| 6,292,526 | B1 | 9/2001 | Patch | 378/4 |
| 6,324,243 | B1 | 11/2001 | Edic et al. | 378/4 |
| 6,353,653 | B1 * | 3/2002 | Edic | 378/8 |
| 6,373,920 | B1 | 4/2002 | Hsieh | 378/98.11 |
| 6,496,560 | B1 | 12/2002 | Lin et al. | 378/62 |
| 6,546,278 | B1 | 4/2003 | Walsh | 600/428 |

OTHER PUBLICATIONS

Wilson et al. (1999), "Perception of Temporally Filtered X-Ray Fluoroscopic Images", Medical Imaging, IEEE Transacions,vol. 18, Issue 1, Jan. 1999, pp 22-31.*

* cited by examiner

*Primary Examiner*—Edward J. Glick
*Assistant Examiner*—Courtney Thomas
(74) *Attorney, Agent, or Firm*—Fletcher Yoder

(57) ABSTRACT

A method for computing volumetric perfusion in a spatially stationary organ using a computed tomography (CT) imaging system includes positioning an area detector such that the area detector encompasses a spatially stationary organ within the field of view of the imaging system for all view angles, operating the CT imaging system in a cine mode to acquire a plurality of projection data representative of the tissue dynamics in the spatially stationary organ, processing the projection data, temporally filtering respective signals from volume elements of the reconstructions of the projection data which are representative of the tissue dynamics and computing the volumetric perfusion in the organ using the temporally filtered signals from volume elements.

15 Claims, 3 Drawing Sheets

METHODS AND APPARATUS FOR COMPUTING VOLUMETRIC PERFUSION

This application is a Continuation in Part of Ser. No. 10/304,380, filed Nov. 26, 2002, now Pat. No. 6,888,914.

BACKGROUND OF THE INVENTION

This invention relates generally to computed tomography (CT) imaging and more particularly to an apparatus and method for computing volumetric perfusion from temporal reconstructions of tissue attenuation characteristics using digital area detector technology.

In at least one known "third generation" CT system, projection data is continually acquired within a limited axial coverage of a patient to adequately measure the uptake and washout of a contrast medium in an organ being imaged. Additionally, as many as sixteen slices of projection data to be acquired, reconstructed, and processed simultaneously for perfusion evaluation can be accomplished using current multi-row detectors. The scanning speed of a known CT system is adequate for sampling of the contrast dynamics of the tissue within a small volume of an organ; however, the scanning speed is inadequate for sampling the contrast dynamics for a whole organ being imaged, such as a brain since helical scanning protocols are necessary.

BRIEF SUMMARY OF THE INVENTION

In one aspect, a method for computing volumetric perfusion in a spatially stationary organ using a computed tomography (CT) imaging system is provided. The method includes positioning an area detector such that the area detector encompasses a spatially stationary organ within the field of view of the imaging system for all view angles, operating the CT imaging system in a cine mode to acquire a plurality of projection data representative of the tissue dynamics in the spatially stationary organ, generating reconstructed data of the contrast dynamics of the tissue using the projection data; temporally filtering respective signals from volume elements of the reconstructed data which are representative of the tissue dynamics, and computing the volumetric perfusion in the organ using the temporally filtered signal from volume elements.

In another aspect, a computed tomography (CT) imaging system for computing volumetric perfusion in a spatially stationary organ is provided. The CT imaging system includes a radiation source, an area detector, and a computer operationally coupled to the radiation source and the area detector. The computer is configured to position an area detector such that the area detector encompasses a spatially stationary organ within the field of view of the imaging system for all view angles, operating the CT imaging system in a cine mode to acquire a plurality of projection data representative of the tissue dynamics in the spatially stationary organ, processing the projection data, generating reconstructed data of the contrast dynamics of the tissue using the projection data, temporally filtering respective signals from volume elements of the reconstructed data which are representative of the tissue dynamics to reduce noise, and computing the volumetric perfusion in the organ using the temporally filtered signals from volume elements.

In a further aspect, a computer readable medium encoded with a program is provided. The medium is configured to instruct a computer to position an area detector such that the area detector encompasses a spatially stationary organ within the field of view of the imaging system for all view angles, operate the CT imaging system in a cine mode to acquire a plurality of projection data representative of the tissue dynamics in the spatially stationary organ, process the projection data, reconstruct the projection data, temporally filter respective signals from volume elements of the reconstructions to reduce noise, and compute the volumetric perfusion in the organ using the filtered signals from volume elements which are representative of the tissue dynamics.

DETAILED DESCRIPTION OF THE INVENTION

Figure 1:
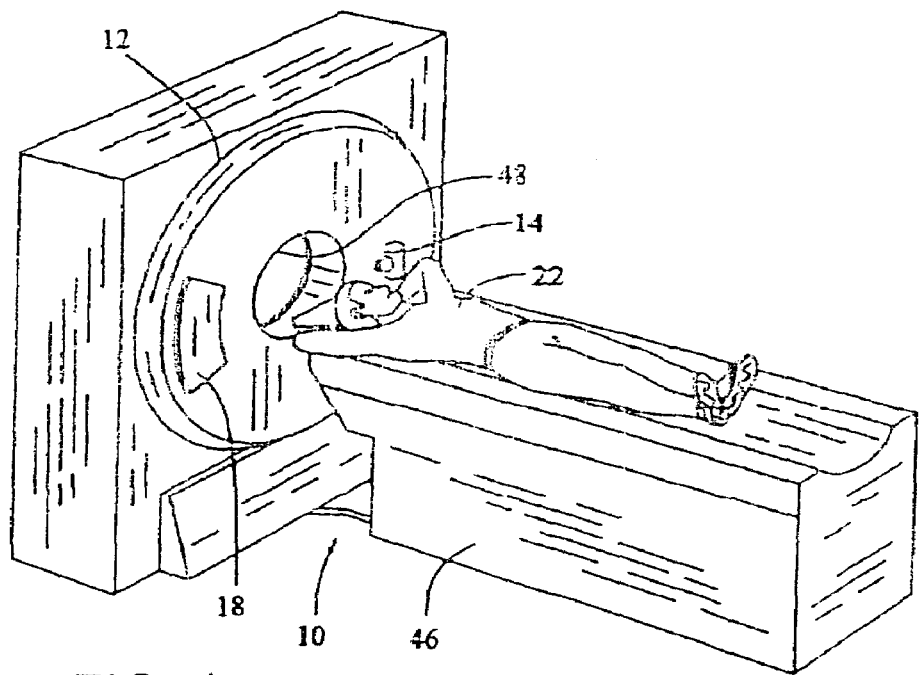
FIG. 1 is a pictorial view of a CT imaging system.

The methods and apparatus described herein address acquiring projection data allowing improved computation of the volumetric perfusion in an organ using area detector technology. Volumetric perfusion refers to the computation of mean transit time, blood volume, and/or blood flow from reconstructions of projection data, or the combination of any of these quantities into one mathematical metric. Methods are described to facilitate reducing CT imaging system constraints such as a gantry scanning speed. In addition, the methods described herein facilitate reducing noise and improving the temporal resolution relative to the gantry scanning speed in contrast enhanced measurements, thereby improving the stability and accuracy of a deconvolution process used in perfusion computations.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector about the object to be imaged.

In an axial scan, the projection data is processed to construct an image that corresponds to a two-dimensional slice taken through the object. One method for reconstructing an image from a set of projection data is referred to in the art as the filtered back-projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
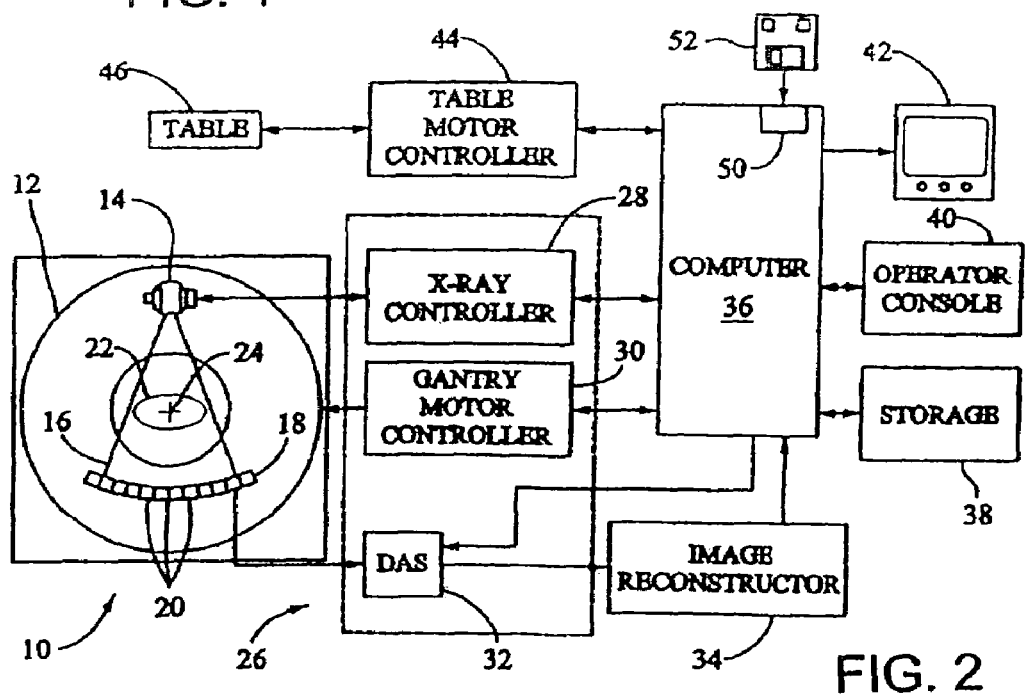
FIG. 2 is a block schematic diagram of the system illustrated in FIG. 1.

Referring to FIGS. 1 and 2, a multi-slice scanning imaging system, for example, a computed tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence allows estimation of the attenuation of the beam as it passes through object or patient 22 when compared to the electrical signal that is measured when no patient is placed in gantry 12. During a scan to acquire x-ray projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan. Moreover, an area detector array 18 includes many rows of detector elements 20 such that projection data corresponding to large volume can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a mass storage device 38. Image reconstructor 34 may be specialized hardware or software operating on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In an embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Additionally, although described in a medical setting, it is contemplated that the benefits of the invention accrue to all CT systems including industrial CT systems such as, for example, but not limited to, a baggage scanning CT system typically used in a transportation center such as, for example, but not limited to, an airport or a rail station.

Figure 3:
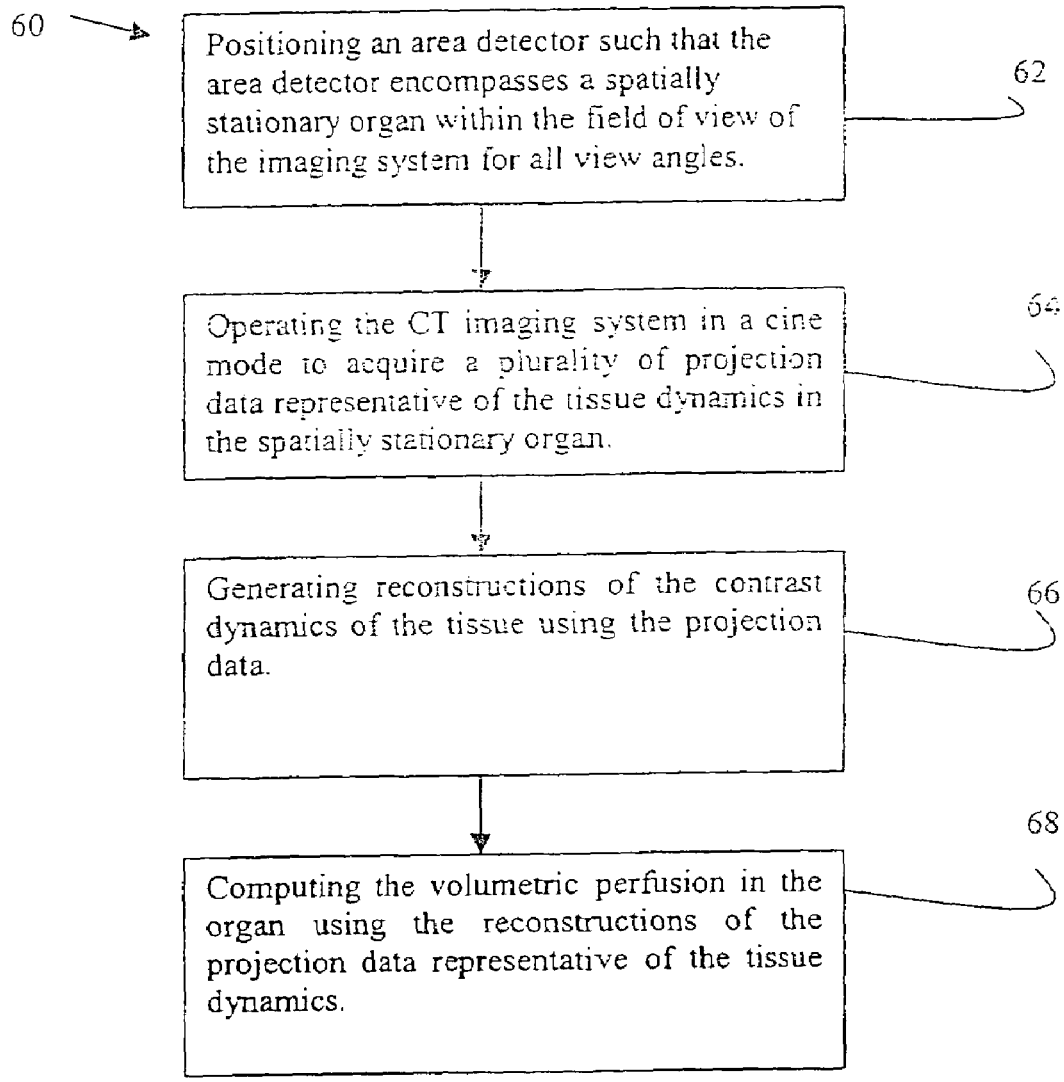
FIG. 3 is a flowchart illustrating a method for computing volumetric perfusion in a spatially stationary organ using a computed tomography (CT) imaging system.

FIG. 3 is a flow chart illustrating a method 60 for computing volumetric perfusion in a spatially stationary organ using computed tomography (CT) imaging system 10. Method 60 includes positioning 62 an area detector 18 such that area detector 18 encompasses a spatially stationary organ within the field of view of the imaging system for all view angles, operating 64 the CT imaging system in a cine mode to acquire a plurality of projection data representative of the tissue dynamics in the spatially stationary organ, generating 66 reconstructions of the contrast dynamics of the tissue using the projection data, and computing 68 the volumetric perfusion in the organ using the reconstructions of the projection data representative of the tissue dynamics.

In use, a spatially stationary organ 22, such as a brain or a liver, for example, is positioned between radiation source 14 and area detector 18 such that area detector 18 encompasses a spatially stationary organ within the field of view of the imaging system for all view angles, i.e. area detector 18 is positioned to encompass a field of view of brain 22 for all view angles. In one embodiment, a plurality of signals emitted from area detector 18 are digitized, and a plurality of rows of area detector 18 are digitized simultaneously such that a sampling frequency of area detector 18 readout is, for example, 120 frames per second. In some area detector readout schemes, if 4 rows of detector data 18 are simultaneously multiplexed into digitizing electronics, 960 views of spatially stationary organ 22, can be acquired per rotation in a 2 second scan. System 10 is operated in a cine mode such that the sampling frequency of the projection data measuring the uptake and washout of a contrast agent in spatially stationary organ 22 at each view position is approximately 1 second when gantry 12, including area detector 18, rotates at a speed of approximately 1 rotation per second.

Accordingly, using sampling theory and the assumption that the projection data at a particular position of gantry 12 have low frequency content and do not violate the Nyquist sampling theorem, the projection data at any instant of time for each of the view angles can be computed and then reconstructed. Therefore, the contrast dynamics in spatially stationary organ 22 being imaged can be computed at any instant of time using the interpolated projection data at each view angle position for a scan. In one embodiment, method 60 is used to itemize the processing steps for at least one known perfusion algorithm. Additionally, volumetric perfusion analysis can be accomplished since area detector 18 measures the projection data for the complete spatially stationary organ 22 simultaneously. In one embodiment, the sampled projection data are temporally filtered and interpolated to any instant of time, thereby facilitating a reduction in noise and an improvement in the temporal resolution of the contrast dynamics using signal processing techniques since a plurality of acquisitions are used to generate the projection data at the particular instance in time.

In an embodiment, a speed of gantry 12 is reduced and the processing steps implemented, thereby facilitating an increase in the views used for reconstruction. In another embodiment, the views for reconstruction can be increased by reducing an axial coverage of area detector 18 by digitizing a fewer quantity of rows, less than the first quantity of rows. In another embodiment, the views for reconstruction can be increased by reducing the axial resolution of area detector 18 by multiplexing and digitizing a quantity of rows greater than the first quantity of rows of area detector data 18.

In an exemplary embodiment, system 10 facilitates computation of volumetric perfusion measurements that include an increased temporal resolution in the reconstruction of contrast dynamics, and an increased signal-to-noise ratio in the projection data, thereby improving the image quality in reconstructed images. System 10 also facilitates an increase in the axial coverage for perfusion computation by using area detector technology. Additionally, projection data are interpolated to a particular instant in time, therefore, temporal averaging of projection data in CT reconstructions is minimized. The signal processing used in the interpolation process to resolve contrast dynamics in projection images also facilitates a reduction in the noise in the measurements.

Figure 4:
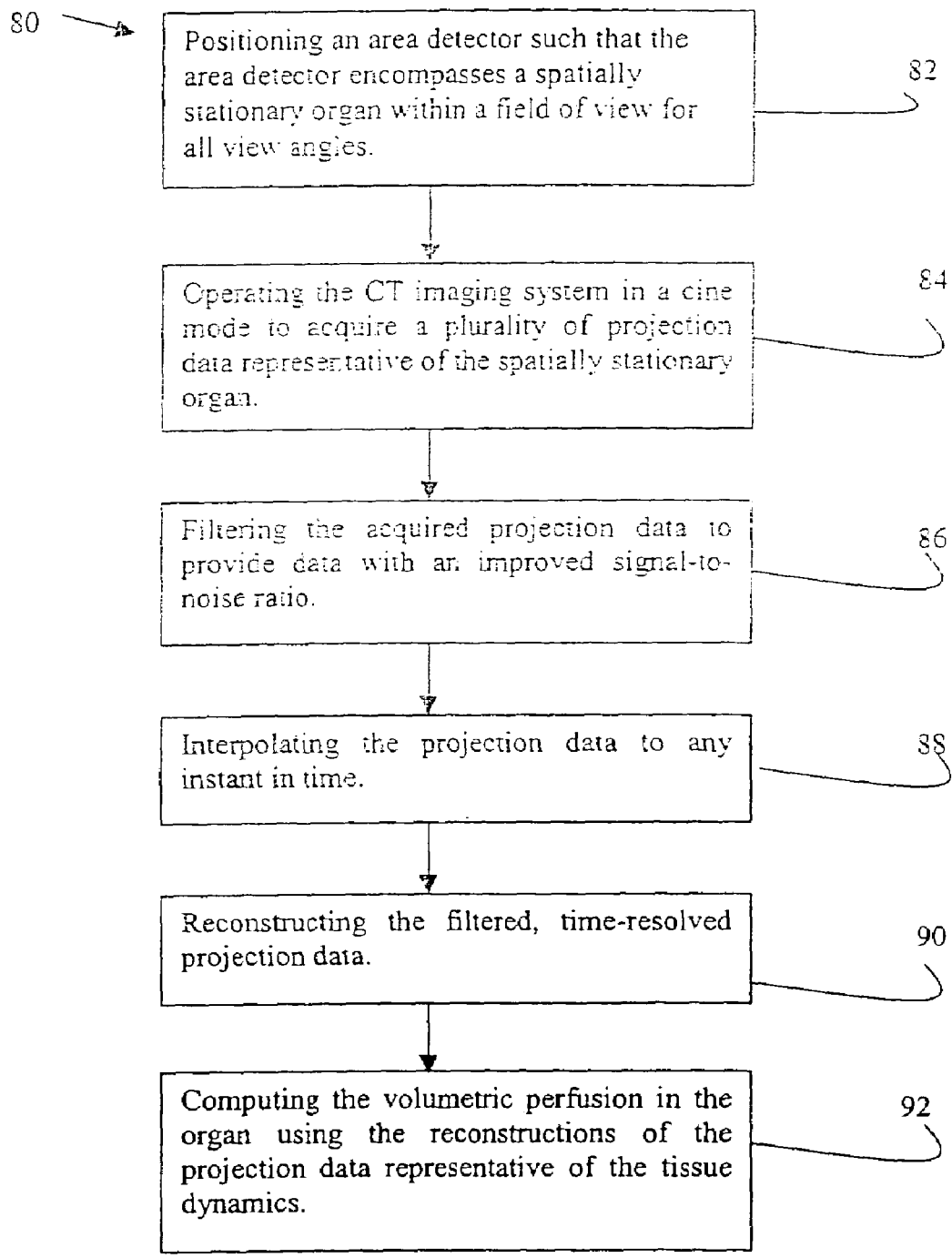
FIG. 4 is a flow chart illustrating a method for obtaining data of a spatially stationary organ using a Computed Tomography (CT) imaging system.

FIG. 4 is a flow chart illustrating a method 80 for obtaining data of a spatially stationary organ using a Computed Tomography (CT) imaging system having a field of view. Method 80 includes positioning 82 an area detector such that the area detector encompasses a spatially stationary organ within a field of view for all view angles, operating 84 the CT imaging system in a cine mode to acquire a plurality of projection data representative of the spatially stationary organ, temporally filtering 86 the acquired projection data to provide data with an improved signal-to-noise ratio, interpolating 88 the projection data to any instant in time, reconstructing 90 the filtered, time-resolved projection data, and computing 92 the volumetric perfusion in the organ using the reconstructions of the projection data representative of the tissue dynamics. Method 80 also includes filtering the acquired projection data at a selected frequency range. Either of the steps of temporally filtering 86 or interpolation 88 in method 80 may be optionally omitted depending on a certain imaging application. For example, interpolation may be unnecessary in certain higher speed acquisition schemes, "higher speed" being defined as equal to or faster than 1 scan or rotation per second.

In an embodiment of the present invention, when interpolation 88 is omitted, the temporal filtering 86 is implemented using the plurality of projection data acquired at each view position. In a further embodiment, due to the linear nature of the mathematical operations involved, the temporal filtering may also be accomplished using the reconstructed data. In the embodiment using reconstructed data, each signal from a volume element or voxel associated with the reconstructed volume is temporally filtered for the plurality of reconstructed data sets. As used herein the terms "signals from a volume element" and "signals from a voxel" refer to intensity values within the three-dimensional (3D) volume. In order to temporally filter reconstructed data, each signal from a voxel within the reconstructed data set is temporally filtered by obtaining the same voxel element within each reconstructed image (i.e. slice at each acquisition time) making up the sequence of reconstructed data. Once obtained, the signal from the voxel is identified and filtering is implemented using one of any known signal processing filter techniques, such as but not limited to Fourier-domain based filtering or convolution filtering. After temporally filtering each of the signals from the voxel elements, the volumetric perfusion is computed using one of any known volumetric perfusion computation techniques. Although it is not possible to reduce the temporal averaging in the reconstructed images by filtering in this manner that would occur if interpolation of the projection data were performed, it is possible to improve the signal-to-noise ratio in the reconstructed images by reducing noise. The previously mentioned advantages of improved signal-to-noise ratio for perfusion assessment apply equally to this processing scheme. A further advantage of filtering as described herein is that the radiation dose applied during imaging is reduced since the same image quality can be generated with images reconstructed with poorer signal-to-noise ratio. By reducing the dose administered to the patient, the signal-to-noise ratio in the measurements is reduced; however, image quality is not sacrificed using the filtering techniques described herein.

Accordingly, system 10 enables enhanced volumetric perfusion measurements, improves temporal resolution in reconstruction of contrast dynamics of human tissue, and improves the signal-to-noise in projection data or reconstructed images, thereby improving image quality in reconstructions, and improving perfusion estimates in human tissue. An additional benefit of the processing methods described by the present invention is that the original resolution of the reconstructed images is maintained.

While the invention has been described in terms of various specific embodiments, those skilled in the art will recognize that the invention can be practiced with modification within the spirit and scope of the claims. Although specific mention of third generation CT imaging systems is incorporated herein, a fourth generation CT system (stationary detector and rotating x-ray source) and a fifth generation CT system (stationary detector and stationary x-ray source) can be used to implement the method, imaging system, and computer readable medium encoded with a program. The signal processing methods described herein may also be used with existing CT systems having limited axial coverage to improve the signal-to-noise ratio in projection data and improve the temporal resolution of the contrast dynamics, thereby improving the image quality in reconstructed images of the contrast dynamics within an organ, such as the brain. Although the temporal filtering and interpolation schemes have been described with reference to projection data, these techniques may be implemented with processed transmission measurements. As used herein, "processed transmission measurements" refer to intensity measurements that have been offset corrected and normalized with a signal representative of the x-ray intensity in air. These methods can be used to reduce the dose of ionizing radiation administered to a patient to improve patient safety, while achieving the same image quality in reconstructed images of the contrast dynamics in tissue within the patient.

What is claimed is:

1. A method for computing volumetric perfusion in a spatially stationary organ using a computed tomography (CT) imaging system having a field of view, said method comprising:
   positioning an area detector such that the area detector encompasses a spatially stationary organ within the field of view of the imaging system for all view angles;
   operating the CT imaging system in a cine mode to acquire a plurality of projection data representative of tissue dynamics in the spatially stationary organ;
   generating reconstructed data of contrast dynamics of tissue using the projection data;
   temporally filtering respective signals from volume elements of the reconstructed data, the signals from volume elements being representative of the tissue dynamics; and
   computing the volumetric perfusion in the organ using the temporally filtered signals from volume elements.

2. A method in accordance with claim 1, wherein the filtering step is adapted to reduce noise in images to allow a reduction in radiation dose applied during imaging.

3. A method in accordance with claim 1, wherein the filtering step is adapted to reduce noise.

4. A computed tomography (CT) imaging system for computing volumetric perfusion in a spatially stationary organ comprising:
   a radiation source;
   an area detector; and
   a computer operationally coupled to said radiation source and said area detector, said computer configured to:
   position the area detector such that the area detector encompasses the spatially stationary organ within a field of view of the imaging system for all view angles;
   operate the CT imaging system in a cine mode to acquire a plurality of projection data representative of tissue dynamics in the spatially stationary organ;
   generate reconstructed data of contrast dynamics of tissue using the projection data; and
   temporally filter respective signals from volume elements of the reconstructed data to reduce noise, the signals from volume elements being representative of the tissue dynamics; and
   compute the volumetric perfusion in the organ using the temporally filtered signals from volume elements.

5. A CT imaging system in accordance with claim 4, wherein the computer filters the reconstructed data to reduce noise in images and allows a reduction in radiation dose applied during imaging.

6. A computer readable medium encoded with a program configured to instruct a computer to:
   position an area detector such that the area detector encompasses a spatially stationary organ within a field of view of a computed tomography (CT) imaging system for all view angles;
   operate the CT imaging system in a cine mode to acquire a plurality of projection data representative of tissue dynamics in the spatially stationary organ;
   generate reconstructions of contrast dynamics of tissue using the projection data;
   temporally filter respective signals from volume elements of the reconstructions to reduce noise, the signals from the volume elements being representative of the tissue dynamics; and
   compute volumetric perfusion in the organ using the temporally filtered signals from the volume elements.

7. A computer readable medium in accordance with claim 6, further encoded to filter the volume elements to allow a reduction in radiation dose applied during imaging.

8. A method for computing volumetric perfusion in a spatially stationary organ using a computed tomography (CT) imaging system having a field of view, said method comprising:
   positioning an area detector such that the area detector encompasses the spatially stationary organ within the field of view of the imaging system for all view angles;
   operating the CT imaging system in a cine mode to acquire a plurality of processed transmission measurements representative of tissue dynamics in the spatially stationary organ;
   filtering the processed transmission measurements at each view angle to reduce noise in the measurements, thereby enabling generation of projection data with improved signal-to-noise ratio;
   generating reconstructions of contrast dynamics of tissue using the projection data; and
   computing the volumetric perfusion in the organ using the reconstructions representative of the tissue dynamics.

9. A method in accordance with claim 8, wherein filtering the processed transmission measurements at each view angle reduces noise and allows a reduction in a radiation dose applied to a patient.

10. A method in accordance with claim 8, further comprising interpolating the plurality of processed transmission measurements to a particular instant in time, thereby enabling generation of reconstructions with improved temporal resolution.

11. A computed tomography (CT) imaging system for computing volumetric perfusion in a spatially stationary organ comprising:
   a radiation source;
   an area detector; and
   a computer operationally coupled to said radiation source and said area detector, said computer configured to:
   position the area detector such that the area detector encompasses the spatially stationary organ within a field of view of the imaging system for all view angles;
   operate the CT imaging system in a cine mode to acquire a plurality of processed transmission measurements representative of tissue dynamics in the spatially stationary organ;
   filter the processed transmission measurements at each view angle to reduce noise, thereby enabling generation of projections with improved signal-to-noise ratio;
   generate reconstructions of contrast dynamics of tissue using the projections; and
   compute the volumetric perfusion in the organ using the reconstructions representative of the tissue dynamics.

12. A CT imaging system in accordance with claim 11, wherein filtering the processed transmission measurements at each view angle to reduce noise allows a reduction in a radiation dose applied to a patient.

13. A CT imaging system in accordance with claim 11, further comprising interpolating the plurality of processed transmission measurements to a particular instant in time, thereby enabling generation of reconstructions with improved temporal resolution.

14. A method for computing volumetric perfusion in a spatially stationary organ using a computed tomography (CT) imaging system having a field of view, said method comprising:
- positioning an area detector such that the area detector encompasses the spatially stationary organ within the field of view of the imaging system for all view angles;
- operating the CT imaging system in a cine mode to acquire a plurality of processed transmission measurements representative of tissue dynamics in the spatially stationary organ;
- interpolating the processed transmission measurements at each view angle to a particular instant in time, thereby enabling generation of time-resolved projection data;
- generating reconstructions of contrast dynamics of tissue using the time-resolved projection data; and
- computing the volumetric perfusion in the organ using the reconstructions representative of the tissue dynamics.

15. A computed tomography (CT) imaging system for computing volumetric perfusion in a spatially stationary organ comprising:
- a radiation source;
- an area detector; and
- a computer operationally coupled to said radiation source and said area detector, said computer configured to:
- position the area detector such that the area detector encompasses the spatially stationary organ within a field of view of the imaging system for all view angles;
- operate the CT imaging system in a cine mode to acquire a plurality of processed transmission measurements representative of tissue dynamics in the spatially stationary organ;
- interpolate the processed transmission measurements at each view angle to a particular instant in time, thereby enabling generation of time-resolved projection data;
- generate reconstructions of contrast dynamics of tissue using the time-resolved projection data; and
- compute the volumetric perfusion in the organ using the reconstructions representative of the tissue dynamics.

* * * * *